(12) United States Patent
Prasad et al.

(10) Patent No.: US 10,045,731 B2
(45) Date of Patent: Aug. 14, 2018

(54) DEVICE AND APPARATUS TO FACILITATE CERVIX CANCER SCREENING

(71) Applicant: M/S. Manipal University, Manipal (IN)

(72) Inventors: Keerthana Prasad, Udupi (IN); Shyamala Guruvare, Udupi (IN); Suma Nair, Manipal (IN); Harishchandra Hebbar N, Manipal (IN); Vidya Kudva, Karkala (IN); Roopa Hegde, Karkala (IN)

(73) Assignee: M/S MANIPAL UNIVERSITY, Karnataka (IN)

( * ) Notice: Subject to any disclaimer, the term of this patent is extended or adjusted under 35 U.S.C. 154(b) by 0 days.

(21) Appl. No.: 15/113,843

(22) PCT Filed: Jun. 22, 2016

(86) PCT No.: PCT/IN2016/000160
§ 371 (c)(1),
(2) Date: Jul. 25, 2016

(87) PCT Pub. No.: WO2016/207906
PCT Pub. Date: Dec. 29, 2016

(65) Prior Publication Data
US 2018/0116581 A1 May 3, 2018

(30) Foreign Application Priority Data
Jun. 25, 2015 (IN) .............................. 3202/CHE/2015

(51) Int. Cl.
*A61B 1/32* (2006.01)
*A61B 5/00* (2006.01)
(Continued)

(52) U.S. Cl.
CPC ........ *A61B 5/4331* (2013.01); *A61B 1/00009* (2013.01); *A61B 1/00048* (2013.01);
(Continued)

(58) Field of Classification Search
CPC ......... G06T 7/0012; G06T 2207/30096; A61B 5/4331; A61B 1/303; A61B 1/00048;
(Continued)

(56) References Cited

U.S. PATENT DOCUMENTS

| | | | | |
|---|---|---|---|---|
| 6,277,067 B1* | 8/2001 | Blair | ................... | A61B 1/00041 348/77 |
| 7,749,162 B2* | 7/2010 | Balas | ..................... | A61B 1/303 600/220 |

(Continued)

*Primary Examiner* — Pedro Philogene

(57) ABSTRACT

An apparatus for detecting cervical cancer comprising, a mechanical structure configured to expose cervical region comprising, a first duck-billed blade forming a hollow cylinder at one end and a second duck-billed blade coupled to the first blade to form part of a speculum, in that the cervical region is exposed through circular area of the hollow cylinder, a pair of "L" shaped rods attached to the hollow cylinder of the first blade such that they are diagonally opposite and symmetric on either side of the exposed cervical region, and a detachable holder with a housing to hold a secondary unit and at least a pair of hooks to mount on the "L" shaped rods, the secondary unit further comprising, a camera for capturing an image of the exposed cervical region, a processor and a visual indicator to determine and indicate presence or absence of the cervix cancer from the image.

3 Claims, 11 Drawing Sheets

(51) Int. Cl.
- *A61B 1/00* (2006.01)
- *A61B 1/303* (2006.01)
- *G06T 7/00* (2017.01)
- *A61B 17/42* (2006.01)

(52) U.S. Cl.
CPC .......... *A61B 1/00105* (2013.01); *A61B 1/303* (2013.01); *G06T 7/0012* (2013.01); *A61B 1/00052* (2013.01); *A61B 2017/4225* (2013.01); *G06T 2207/30096* (2013.01)

(58) Field of Classification Search
CPC . A61B 1/00105; A61B 1/00052; A61B 17/00; A61B 2017/4225; A61B 1/00009
USPC ............. 600/219–221, 225–229, 268; 606/7, 606/14–17; 435/285.3; 604/109
See application file for complete search history.

(56) References Cited

U.S. PATENT DOCUMENTS

| | | | |
|---|---|---|---|
| 9,877,644 B2 * | 1/2018 | Greenstein | A61B 1/32 |
| 2009/0034824 A1 * | 2/2009 | Li | G06T 7/0012 |
| | | | 382/133 |
| 2009/0076368 A1 * | 3/2009 | Balas | A61B 1/00149 |
| | | | 600/407 |

* cited by examiner

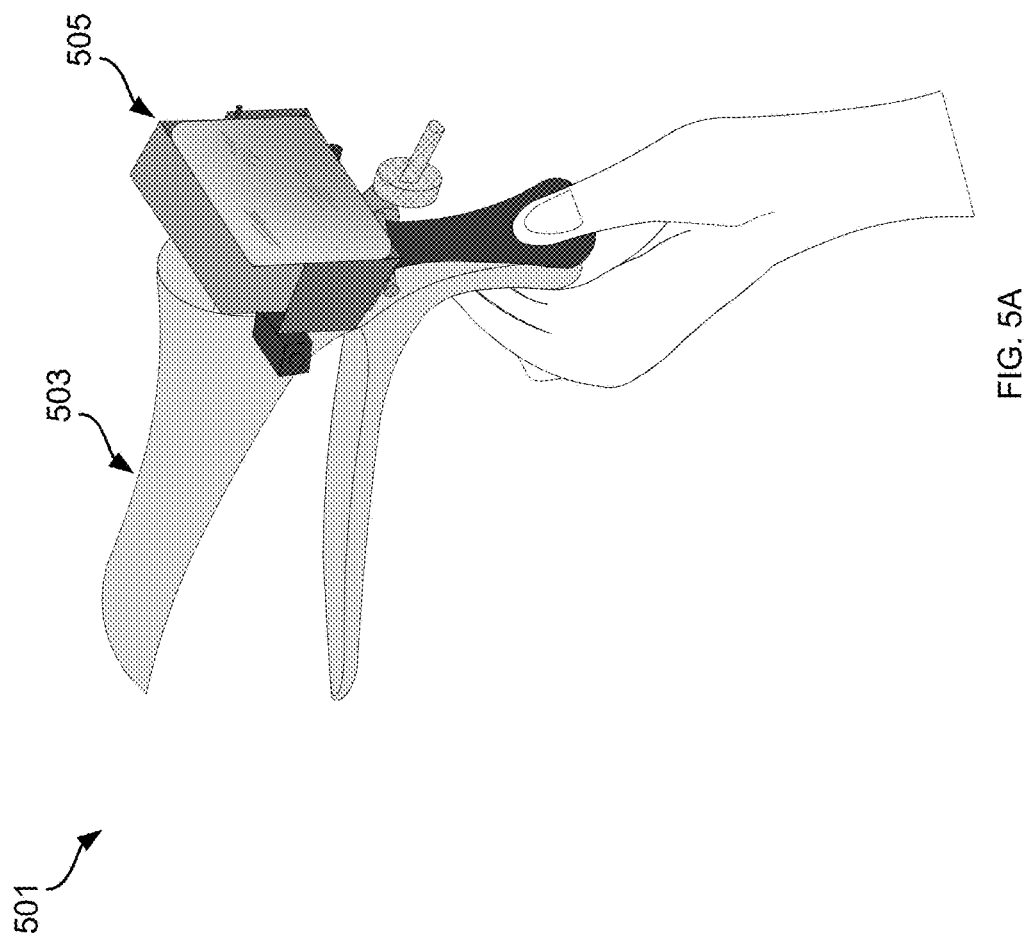

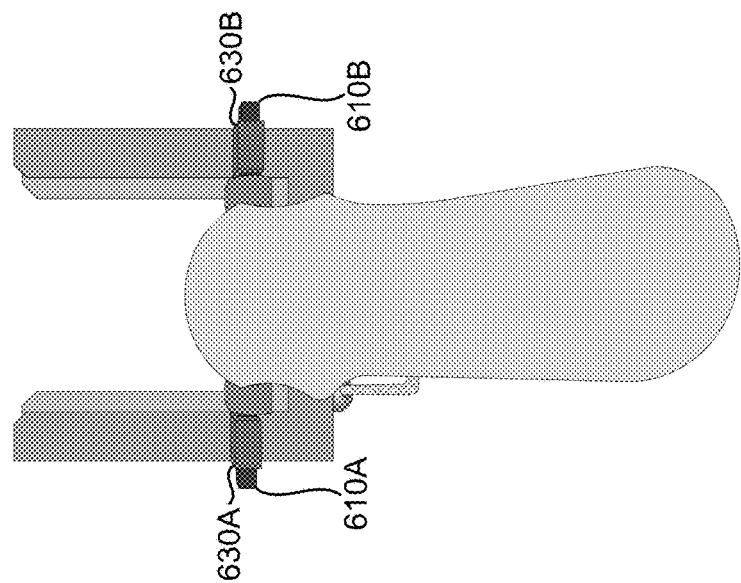
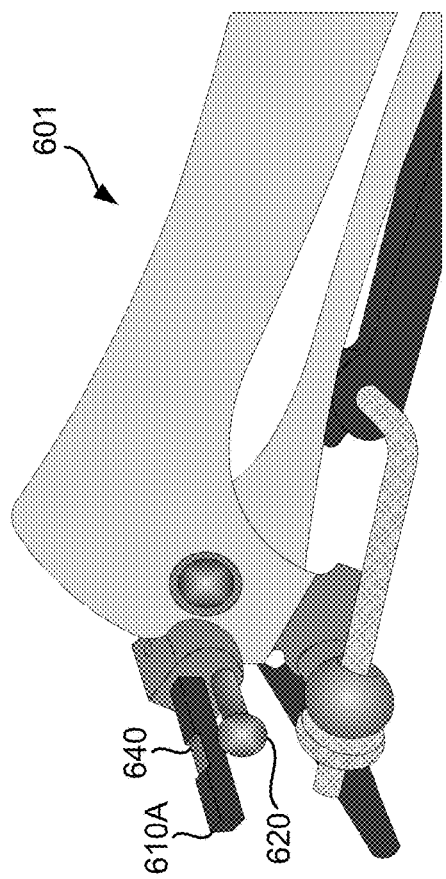
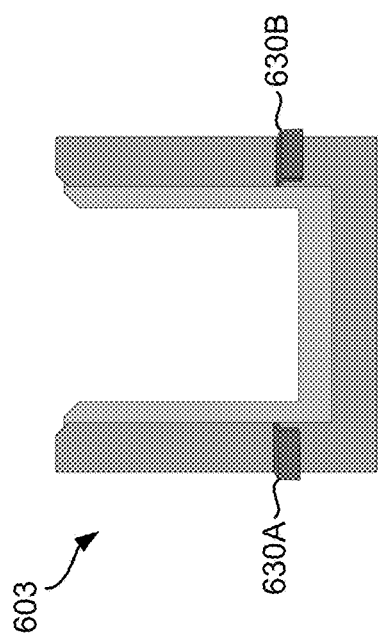
FIG. 6A
FIG. 6B
FIG. 6C

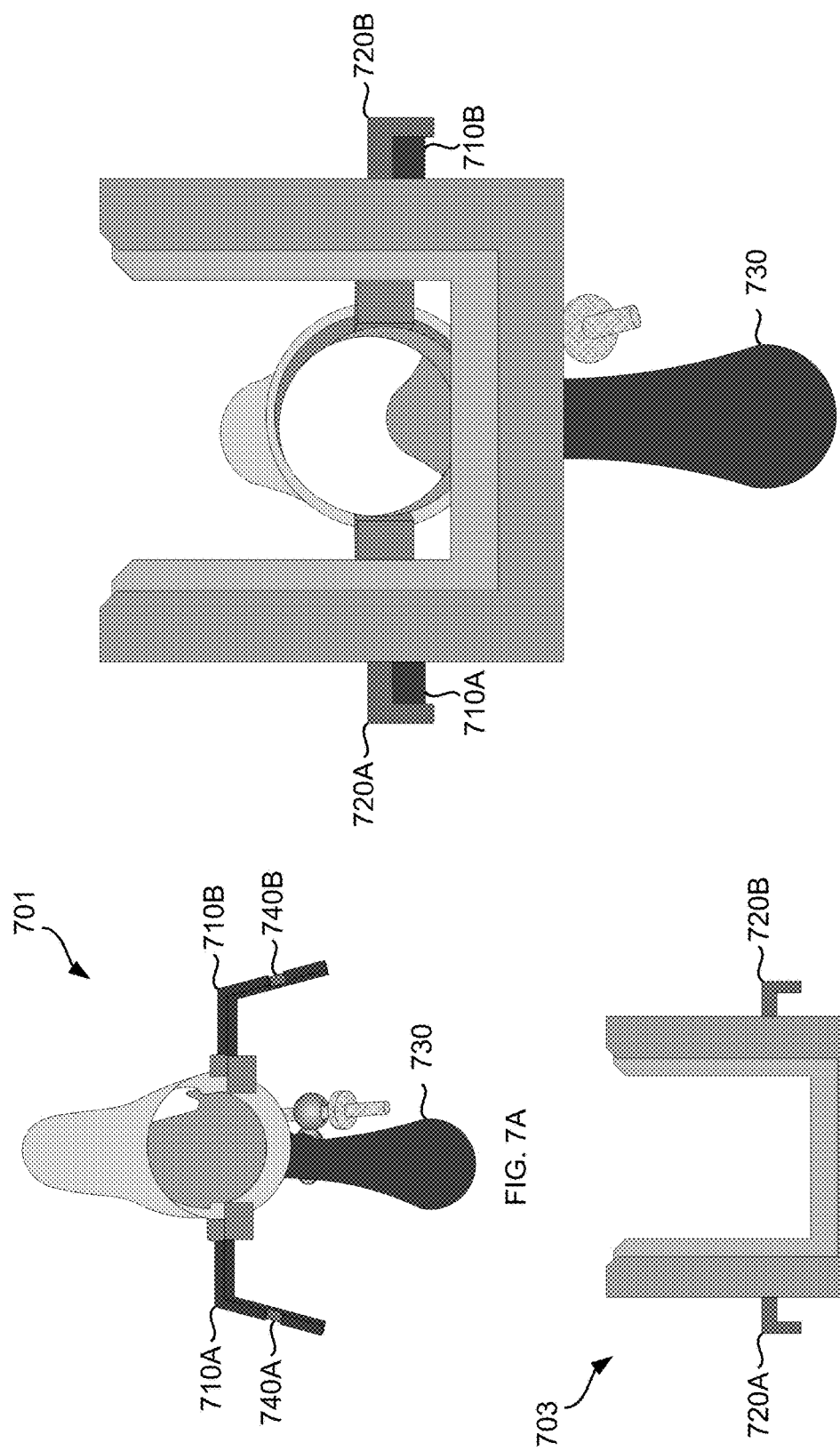

DEVICE AND APPARATUS TO FACILITATE CERVIX CANCER SCREENING

CROSS REFERENCES TO RELATED APPLICATIONS

This application claims priority from Indian patent application No. 3202/CHE/2015 filed on Jun. 25, 2015 which is incorporated herein in its entirety by reference.

BACKGROUND

Technical Field

Embodiments of the present disclosure relate generally to a cancer screening device and more specifically to a device and apparatus that facilitates cervix cancer screening.

Related Art

Cervical cancer is one of the dreadful diseases that occur in women when abnormal cells on cervix grow out of control. It is entirely preventable if found in its early stages of growth. However, there are no organized screening activities in various parts of the world which leads to substantially 85% of deaths in developing nations due to this disease.

There may be various factors accounting to the limitations in detecting cervical cancer at its early stages for example, lack of awareness, inadequate infrastructure, limited accessibility to advanced healthcare delivery system and the like.

Conventionally, early detection of cervical cancer is accomplished by performing regular Pap tests (or cervical smears) which helps in determining abnormal changes in cells of the cervix. This involves in-vitro examination of the cells under microscope which is a tedious process and is further difficult to get a desired tissue biopsy. Also it results in patient inconvenience as it takes several hours while obtaining the desired tissue biopsy for cancer screening process.

Contrary to the in-vitro screening tests, visual inspection of cervix with application of an acid for example, acetic acid or iodine is proved to be a simple and cost effective approach for early detection of cervix cancer. However, this approach has its own limitations for example, lack of skilled or trained manpower, subjective decision of an examiner, inaccurate results while examining with naked eye, lack of documentation for future purposes and the like.

Hence it is necessary for an alternate approach to the conventional techniques for screening cervical cancer providing immediate and accurate results without any requirement of the trained manpower.

SUMMARY

According to an aspect of the present disclosure, an apparatus for detecting cervical cancer comprising a mechanical structure configured to expose cervical region comprising a supporting rod, and an image capturing unit to capture cervix images and determine abnormalities in the cervix region based on preprogrammed instructions, wherein the image capturing unit is coupled to the mechanical structure on the supporting rod. The image capturing unit is coupled to the mechanical structure by means of a detachable unit mounted on the supporting rods of the mechanical structure.

In an embodiment, the detachable unit comprises a housing to hold the image capturing unit and at least a pair of extension hooks outside its peripheral surface to mount on the supporting rods securely. The image capturing unit captures plurality of images before and after application of a chemical substance on the cervix region and determines abnormalities based on temporary change in color and texture of the cervix region due to application of the chemical substance.

According to another aspect of the present disclosure, the mechanical structure comprises a pair of duck-billed blades forming a speculum in which a hollow circular end of a first blade is coupled to flat end of a second blade, a handle coupled to the hollow circular end of the first blade and the flat end of the second blade by a hinge, a rotating screw coupled to the handle for securing the first and second blades in a desired position and at least one supporting rod coupled to either sides of the circular end of the first blade, wherein pressing the handle towards the flat end of the second blade moves the first and second blades to widen vaginal walls and expose cervix region through the hollow circular end of the first blade.

Several embodiments are described below, with reference to the diagrams for illustration. It should be understood that numerous specific details are set forth to provide a full understanding of the invention. One skilled in the relevant art, however, will readily recognize that embodiments may be practiced without one or more of the specific details, or with other methods, etc. In other instances, well-known structures or operations are not shown in detail to avoid obscuring the features of the invention.

BRIEF DESCRIPTION OF DRAWINGS

FIG. 5A is a schematic diagram illustrating the device comprising primary unit and the secondary unit facilitating screening of the cancer cervix in an embodiment of the present disclosure.

FIG. 6A through 6C are the schematic diagrams illustrating an exemplary setup of the device in another embodiment of the present disclosure.

FIG. 7A through 7C are the schematic diagrams illustrating another exemplary setup of the device in yet another embodiment of the present disclosure.

DETAILED DESCRIPTION OF THE PREFERRED EXAMPLES

FIG. 1A through 1E are the block diagrams illustrating the screening of cervix cancer by using a device disclosed in the present disclosure. The device of the present disclosure provides instantaneous results whether the captured images represent a normal cervix or potentially cancerous lesions requiring escalation to a trained specialist for further investigations. FIG. 1A through 1D are the schematic diagrams illustrating the device comprising a primary/first unit 101, a secondary unit 103 coupled to the primary unit 101, insertion of the primary unit 101 into vaginal canal and attaching or detaching the secondary unit as per requirement respectively.

The primary unit 101 comprises a tool used for direct inspection of the cervix region whereas the secondary unit comprises an image capturing and processing unit to determine abnormality in the cervix region. In an embodiment, the primary unit comprises a pair of duck-billed blades hinged to open and close together forming a speculum and is coupled to the secondary unit by means of a supporting rod. Further a rotating screw is provided to the primary unit for locking the blades in a desired position. The primary unit coupled with the secondary unit helps in instantaneous results of screening the cervix cancer.

Figure 1A:
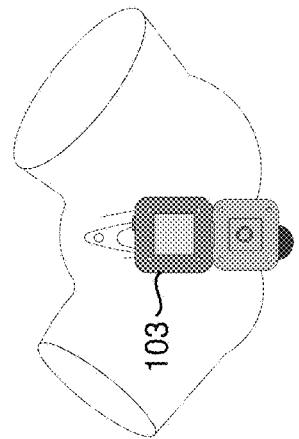
FIG. 1A through 1E are the block diagrams illustrating the screening of cervix cancer by using a device disclosed in the present disclosure.
Figure 1B:
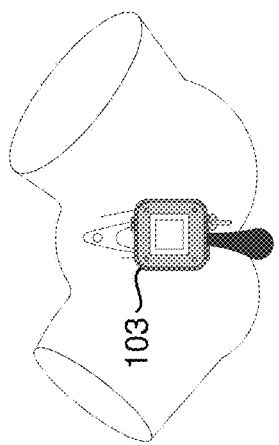
Figures 1C, 1D:
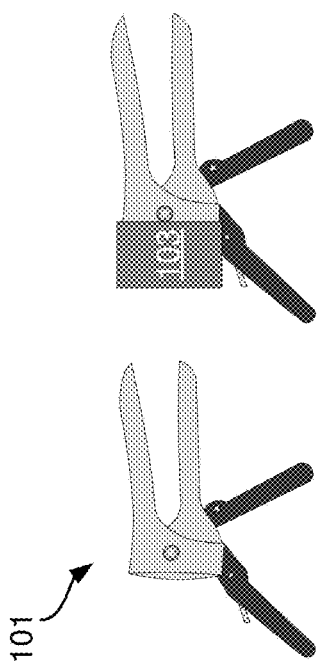

In an embodiment, the secondary unit is detachable from the primary unit for application of a chemical solution comprising dilute acetic acid, iodine and the like on the cervix region as shown in the FIG. 1D. In another embodiment, the entire holder hosting the secondary unit may be detached from the supporting rods of the primary unit as desired. In yet another embodiment, the secondary unit may be opened or closed on the primary unit without disturbing their positions. However, the secondary unit needs to reposition into its active position on the primary unit for further analysis after application of the chemical solution.

Figure 1E:
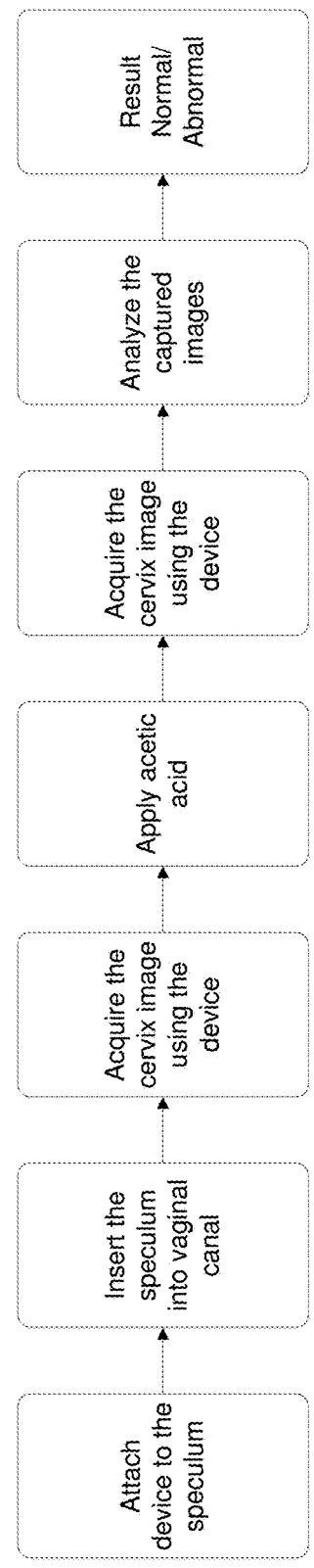

FIG. 1E is a block diagram illustrating the steps involved in screening the cervical cancer by using the device of the present disclosure. The screening process of the cervical cancer comprises initial step of identifying the cervix region by using the primary unit. In an embodiment, the primary unit is inserted into the vaginal canal carefully by a trained specialist to achieve a clear visible cervix region. Then the secondary unit is mounted on the supporting rods of the primary unit. After mounting the secondary unit onto the primary unit, a power management unit of the secondary unit is turned on to provide power for performing a desired operation. The secondary unit is further provided with an illumination source to see the cervix region clearly. In an embodiment, the illumination source comprises a flash light that may be turned on/off as per requirement. By using the image capturing unit of the secondary unit, cervix images are captured with the help of the flash light. In another embodiment, the secondary unit is provided with at least one of touch or voice or gesture control mechanism to perform various operations for example, capturing images, zoom in/out, store, delete, process and the like.

In yet another embodiment, handle of the primary unit is provided with an operative knob at its top by coupling the knob to physical buttons on the secondary unit to control and achieve desired operation. The physical buttons on the secondary unit comprises, but not limited to capture image, zoom in/out, power on/off, flash on/off and the like.

The captured images are then stored into the memory system provided within the secondary unit which are further used as a standard to subsequent captured images while determining abnormality or cancerous lesions in a specific region of the cervix. In an embodiment, the secondary unit is coupled to the primary unit in such a way that it is able to attach or detach from the primary unit to achieve a desired operation as shown in the FIG. 1D. This helps in application of a chemical substance onto the cervix region through primary unit without disturbing its orientation and position.

After application of the chemical substance, again cervix region is captured by the secondary unit and is compared to the standard (image captured before application of the chemical substance) that is stored in the memory. In an embodiment, the cervix region after application of the chemical substance is captured and then the secondary unit is detached from the holder of the primary unit to make the patient more comfortable. The device processes and analyzes the captured images before and after application of the chemical substance to determine cancerous lesions in the cervix region.

The device analyzes and provides a result comprising whether the region of interest captured is normal or abnormal. In an embodiment, an LED indicator is provided with distinguished colors to represent normal, abnormal/cancerous cervix region or no data found. The LED indicator indicating no data found is obtained when the captured images are not sufficient to analyze or detect the cervix region. This may occur due to many factors comprising swelling and bleeding in the cervix region while capturing the images or any unpredictable external factors. In case of no data found indicator, the cervix region need to be screened again after a substantial period of time using the device of the present disclosure to determine abnormalities in the cervix region.

Figure 2A:
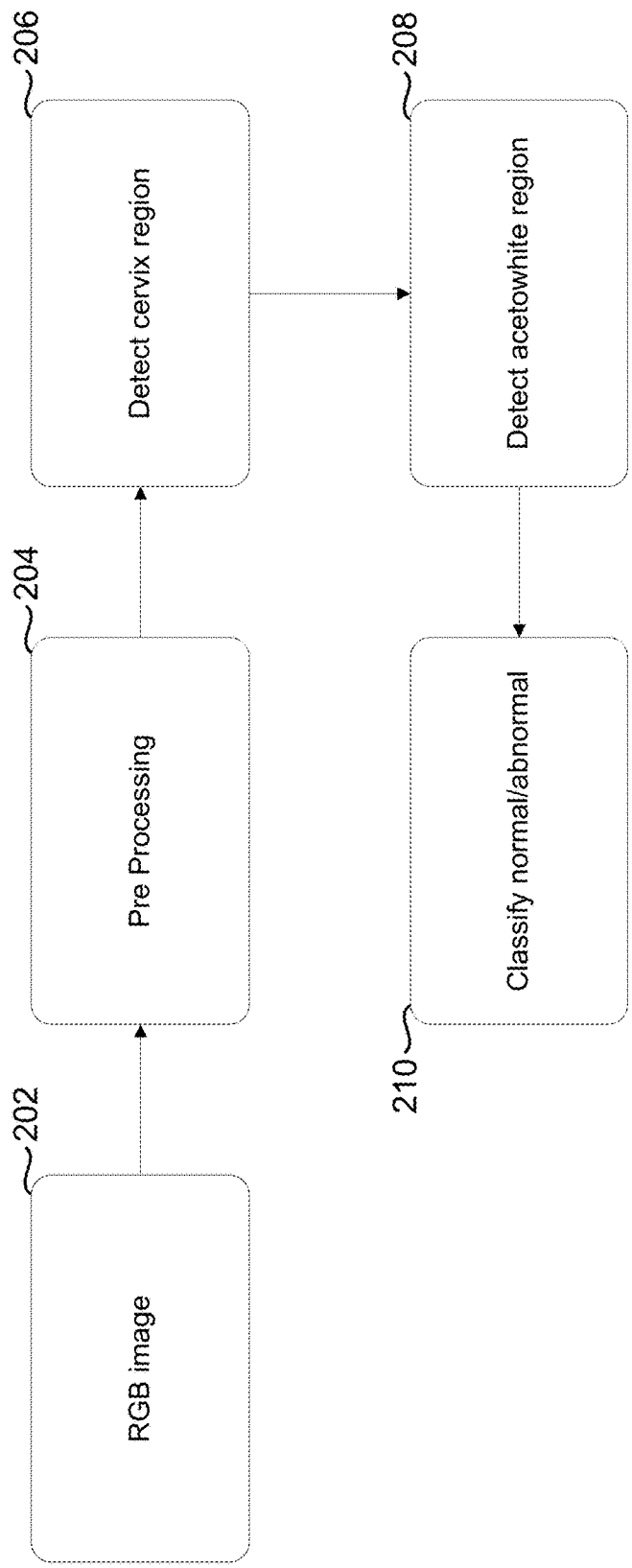
FIG. 2A through FIG. 2D are the block diagrams illustrating the processing of captured images within the device in an embodiment of the present disclosure.

FIG. 2A through FIG. 2D are the block diagrams illustrating the processing of captured images within the device in an embodiment of the present disclosure. FIG. 2A is a block diagram illustrating the steps involved in processing the captured image for cervical cancer screening in an embodiment of the present disclosure.

The image processing of the captured image is based on a phenomenon called acetowhitening wherein the acetowhitening is a temporary white color region observed when cervix surface is applied with a dilute acetic acid. The whitening regions with the application of dilute acetic acid are considered to be as major signs of abnormality. In an embodiment, application of a chemical substance, but not limited to acetic acid, iodine and their derivatives may result in color and texture change of the cervix region and helps in determining abnormalities in a specific region of interest. A pre-installed application within the secondary unit processes the captured images to assess abnormality in the cervix region. The manner in which the captured images are processed by the application is further described in the following figures.

As shown in FIG. 4A, in block 202, a high resolution colored cervix image (RGB image) is acquired from the image capturing unit within the secondary unit. These images are then fed to the preinstalled application comprising the image processing unit. In block 204, the captured RGB image first undergoes preprocessing steps comprising detection and removal of specular reflection (SR), detecting coarse region of interest (ROI) and cervix boundary line.

After preprocessing the captured image, in block 206, the resulting digital image or information from block 204 is then further processed and cropped to a maximum limit depicting substantially the cervix region of interest by removing unwanted regions from the image. In block 208, the region of interest is then analyzed for a color and texture change in region of the cervix to determine abnormalities. In an embodiment, the change in color and texture is analyzed based on the standard provided within the device comprising processed information obtained from the captured images before applying the chemical substance on the cervix region. Based on the change in color and texture of the cervix region, the device provides a result indicating whether the examined region of interest is normal or abnormal.

In an embodiment, the result comprises a set of three light indicators comprising green, yellow and red colors wherein green indicates normal cervix, red indicates the presence of abnormality and yellow indicates the region of interest captured is not sufficient to provide accurate information. The yellow color in the result may occur due to excessive bleeding or unclear captured image.

Figure 2B:
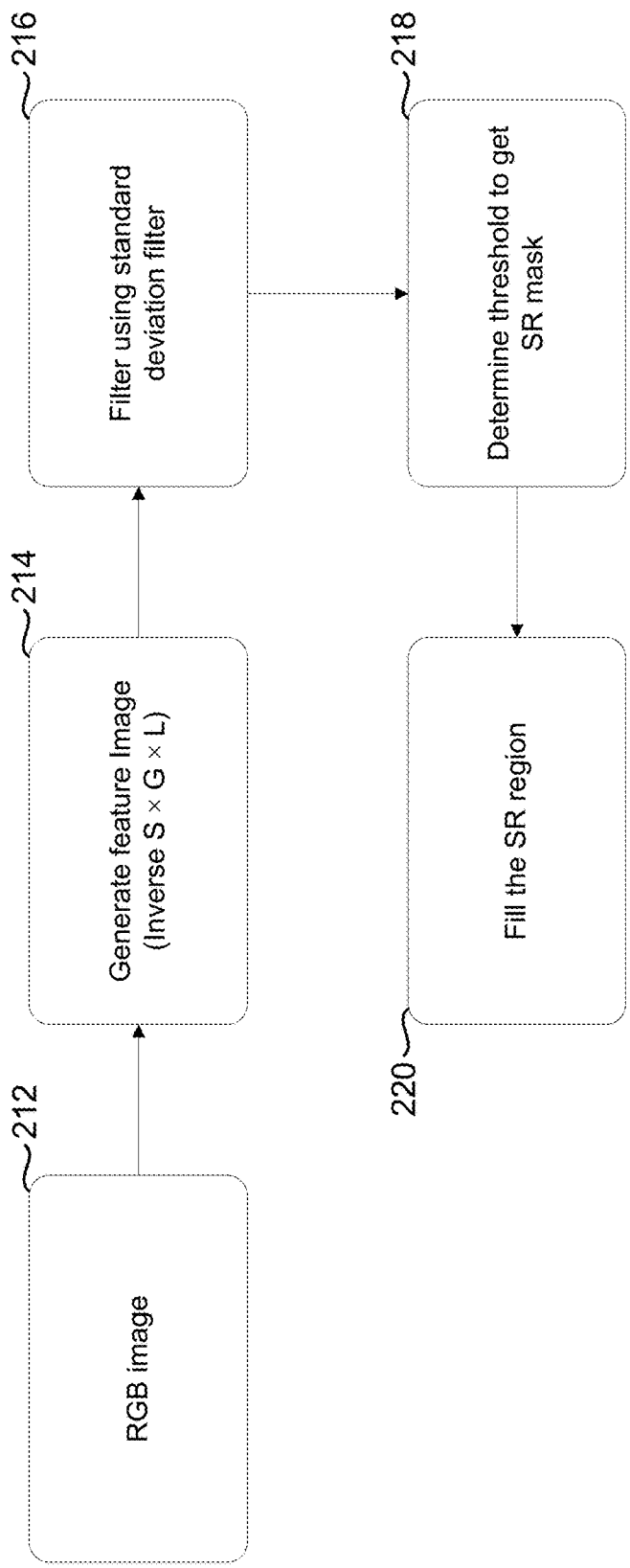

FIG. 2B is a block diagram illustrating the steps involved in detection and removal of specular reflection (SR) in an embodiment of the present disclosure. In block 212, the captured image from the image capturing unit is separated into Red, Green and Blue planes (RGB image). From this image, SR is to be detected and removed for determining the region of interest (ROI).

SR's appear as bright spots heavily saturated with white light causing a major problem in extracting region of interest from the captured image. The SR's occur due to various factors comprising shiny metallic surface of the primary unit, wetness of the cervix region caused by application of the chemical substance and might be the presence of uneven cervix surface, which acts like a mirror reflecting light from an illuminated source. The detection of specular regions comprises two steps viz., detection and filling of SR regions.

Specularities always have very intense brightness (I) and low color saturation (S) values appear to be smooth pixels. In block 214, a feature image is extracted from the RGB image that provides a good glare to background ratio. This feature image may be S and I components of Hue-Saturation-Intensity (HSI) color space of original image, S and V components of Hue-Saturation-Value (HSV) color space of original image, Luminance component (L) of Lab color space or it may even be green component (G) of original RGB image. The obtained feature images may be combined (multiplication, subtraction) to get another feature image. In an embodiment, the S, G and L values are normalized to a range of 0 to 1 and then the multiplication of 1-S, G and L is performed to result a feature image as it provides a good glare to background ratio.

Then a histogram is obtained for the resulting feature image. In an embodiment, the histogram of the feature image takes the shape of normal distribution. Later in block 216, the histogram is further analyzed and filtered by using standard deviation filter. The standard deviation filter calculates standard deviation and assigns this value to center pixel in the output. In an embodiment, firstly the histogram envelops are smoothed in order to remove spikes and then a Gaussian curve is fitted to the smoothened histogram.

Then in block 218, a threshold is determined to detect SR regions of an SR mask. The threshold is selected based on the fact that there are not many pixels that belong to specularities and even less pixels of the same intensity. It is assumed that threshold for all images is somewhere in flat area of the Gaussian curve. Since it is not possible to have one general threshold, using adaptive thresholding is a must. Mean value of the histogram is calculated and threshold is declared to be in the right side of the fitted Gaussian curve whose values are lower than the mean value. The difference in pixel number between consecutive intensity values is determined and threshold is chosen as first intensity that has a difference of five or less pixels.

After determining threshold and pixel values, in block 220, the SR mask is filled with a mean value of non-zero neighboring pixels for complete removal of the SR regions. Initially, the color values of the detected SR pixels are set to zero. For filling of SR region, each pixel inside the SR region is assigned a mean color of its non-zero neighbors in an iterative process. Thus the SR detection and removal process from the RGB image comprises acquiring the feature image from RGB image, obtaining threshold and determining SR mask, making all the pixels of SR region to zero and filling each pixel in the SR region by mean color of its non-zero neighbors until all the SR regions are filled. In yet another embodiment, filling the SR regions is a optional step to obtain a clear image background.

Figure 2C:
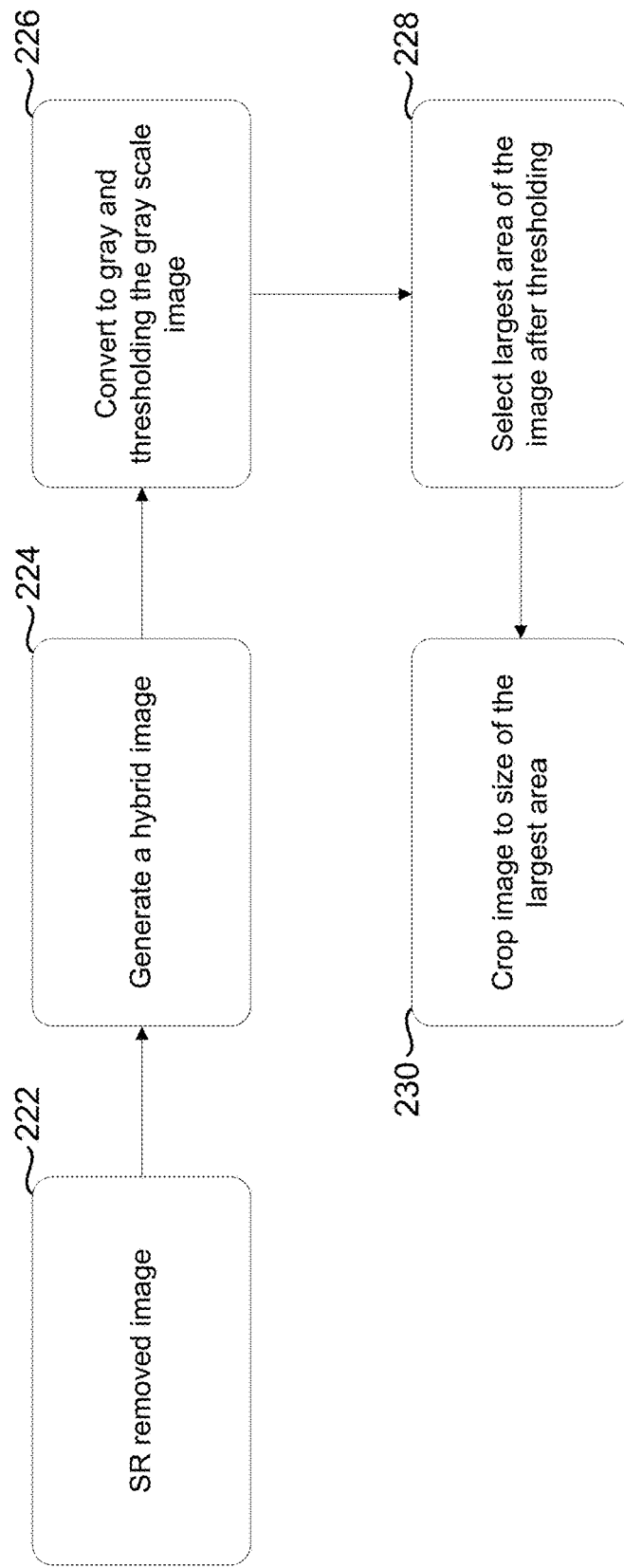

FIG. 2C is a block diagram illustrating the steps involved in detection of coarse region of interest (ROI) in an embodiment of the present disclosure. The ROI detection is based on two aspects in which the cervix color tends to take on red hues in the spectrum and hence it is required to capture the dominant color information from the SR removed image. Another aspect is that cervix region appears to be circular in shape and located substantially at center of the image.

In block 222, the SR removed image is obtained from the block 220 for detecting the region of interest. Then in block 224, a hybrid image is generated from the SR removed image by determining the dominant red color (R) intensity and distance of a pixel from the center of the image. In block 226, the hybrid image is then converted to grayscale and threshold is determined by a simple known image processing technique. Later in block 228, a largest area on the grayscale image after thresholding is selected and retained by discarding the remaining portion of the image. The selected region of the image after thresholding is considered to be as the region of interest where cervix is located. In block 230, the resulting image is further cropped to obtain a rough region of interest by discarding the unwanted pixels from the image as it is considered as noise.

Figure 2D:
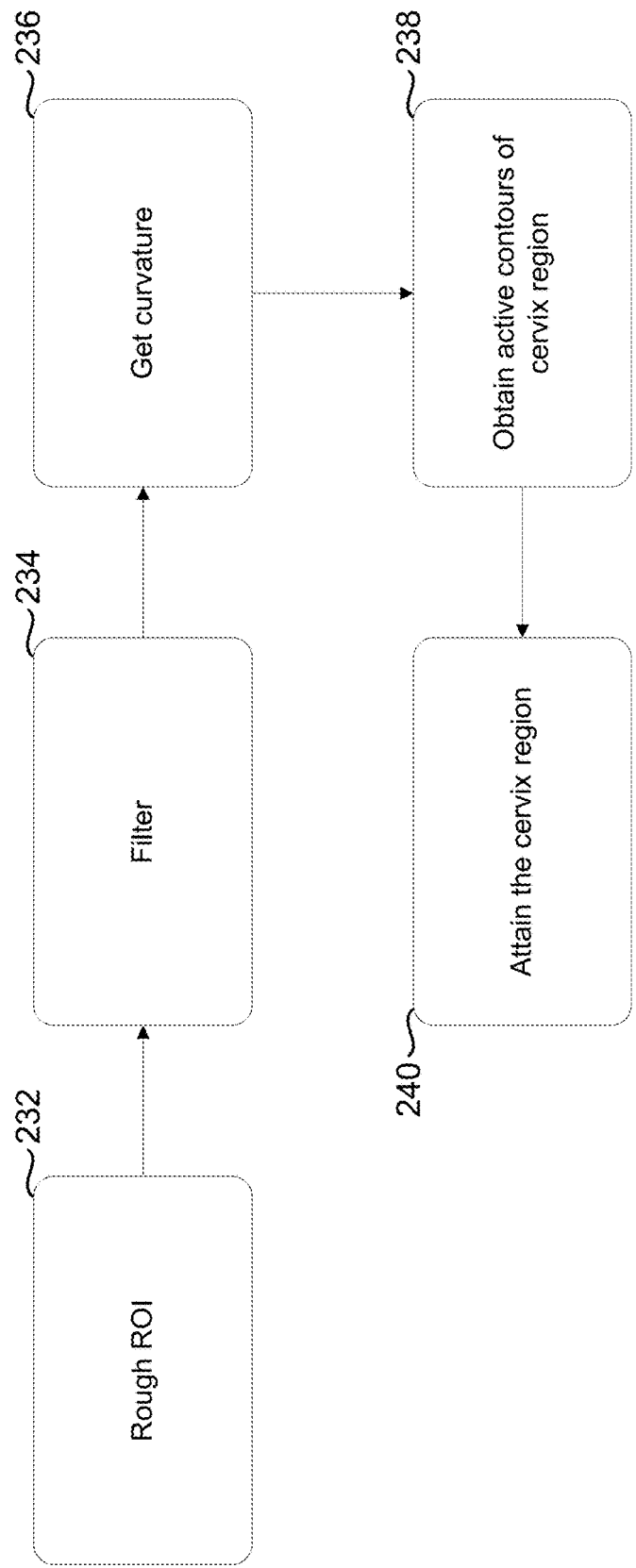

FIG. 2D is a block diagram illustrating the steps involved in detecting boundary of the cervix region from the detected region of interest in an embodiment of the present disclosure. In block 232, the detected rough ROI is further processed to determine exact boundaries of the cervix region to assess abnormality in the cervix. In block 234, the rough region of interest is filtered for noise removal by using a known filter for example, median, Gaussian filters and the like. Then in block 236, an edge operator is applied to the filtered image to detect edges clearly for obtaining a curvature of the cervix region. In block 238, the detected edges are then smoothened by using an appropriate threshold value and removed all undesired pixels to result a thick edge element representing active contours of the cervix region. In block 240, the image within the active contours is cropped and retained by discarding the noise portion or undesired pixels out of the detected active contours to attain the complete region of interest comprising the cervix region.

This region of interest is then analyzed with a standard values and analyzes the change in color and texture of the cervix to determine abnormalities in that region of interest. The standard values comprise the processed information from the image processing unit for the same region of interest before application of the chemical substance. In an embodiment, the device analyzes the change in color and texture by comparing the processed information obtained from corresponding region of interest on the cervix region of the captured RGB image before and after application of the chemical substance.

Figure 3A:
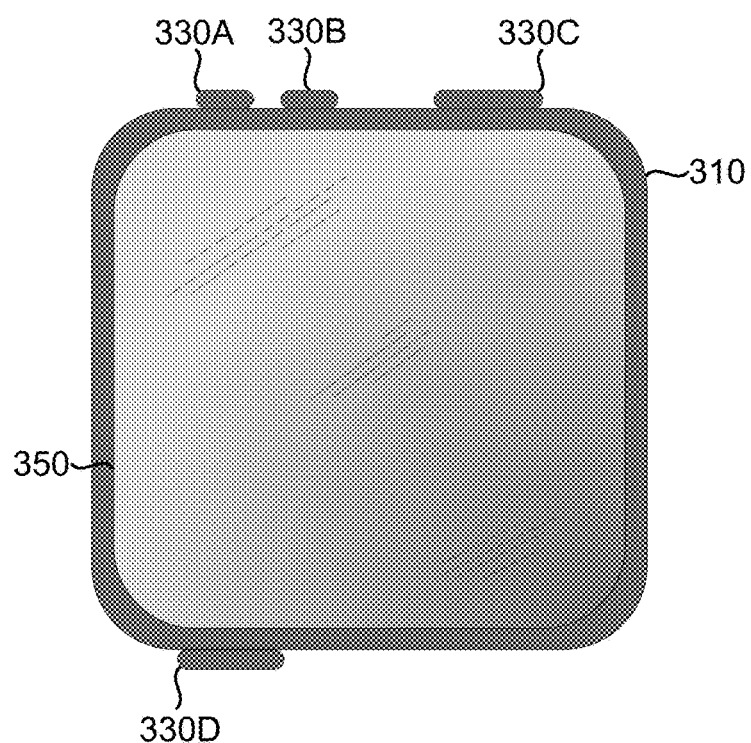
FIG. 3A and FIG. 3B are the block diagrams illustrating the secondary unit of the device in an embodiment of the present disclosure.
Figure 3B:
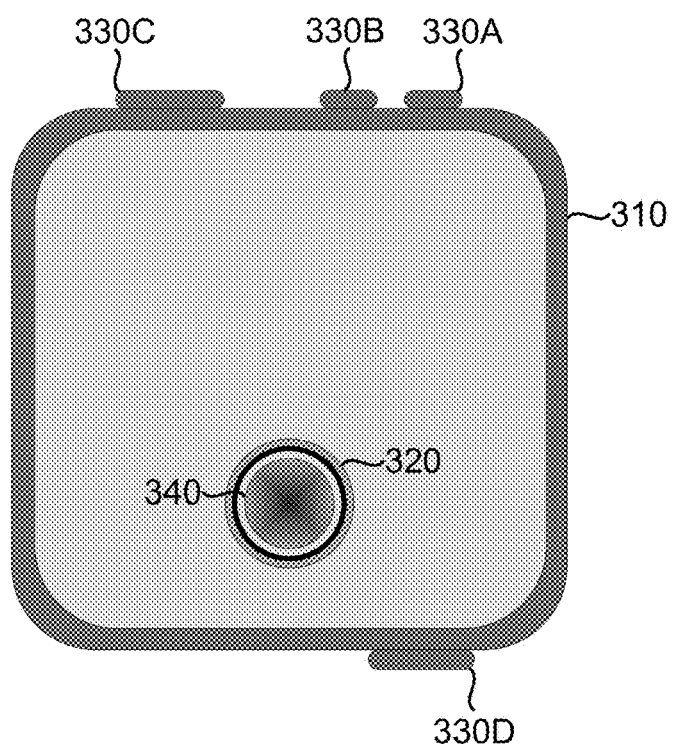

FIG. 3A and FIG. 3B are the block diagrams illustrating the secondary unit of the device in an embodiment of the present disclosure. The secondary unit of the device is able to capture high resolution images and process the captured images to determine abnormalities present in the captured images.

As shown there, the secondary unit comprises an outer body shield 310, portable high resolution camera lens 320 at centre of the outer shield 310, an image sensor with large number of pixels, a lens aperture, a camera shutter 340, a graphical user interface 350 and an image processing unit, wherein the outer shield 310 is provided with manual buttons (330A through 330D) for operating the device. The manual buttons on the secondary unit may comprise, but not limited to capture image, zoom in/out, power on/off, flash on/off and the like. In an embodiment, the secondary unit is provided with a flash light to illuminate the cervix region for capturing clearly visible images.

In an embodiment, the secondary unit captures high resolution images and then uploads the captured images to a preinstalled application within the device. This application then processes the captured image and determines abnormality in the cervix region of the captured image. The abnormality is determined by various factors that may comprise size, shape, texture, color and intensity.

In yet another embodiment, the secondary unit comprises an automatic timer that indicates or alerts user of the device to capture image after application the chemical substance on the cervix region. The timer starts after application of the chemical substance on the cervix region and after a predetermined period of time say, after 1 min it alerts the user to capture another image for determining change in color and texture of the region indicating abnormalities of the cervix region. The primary elements of the secondary unit that are required to operate the device are further described in the following figure.

Figure 4:
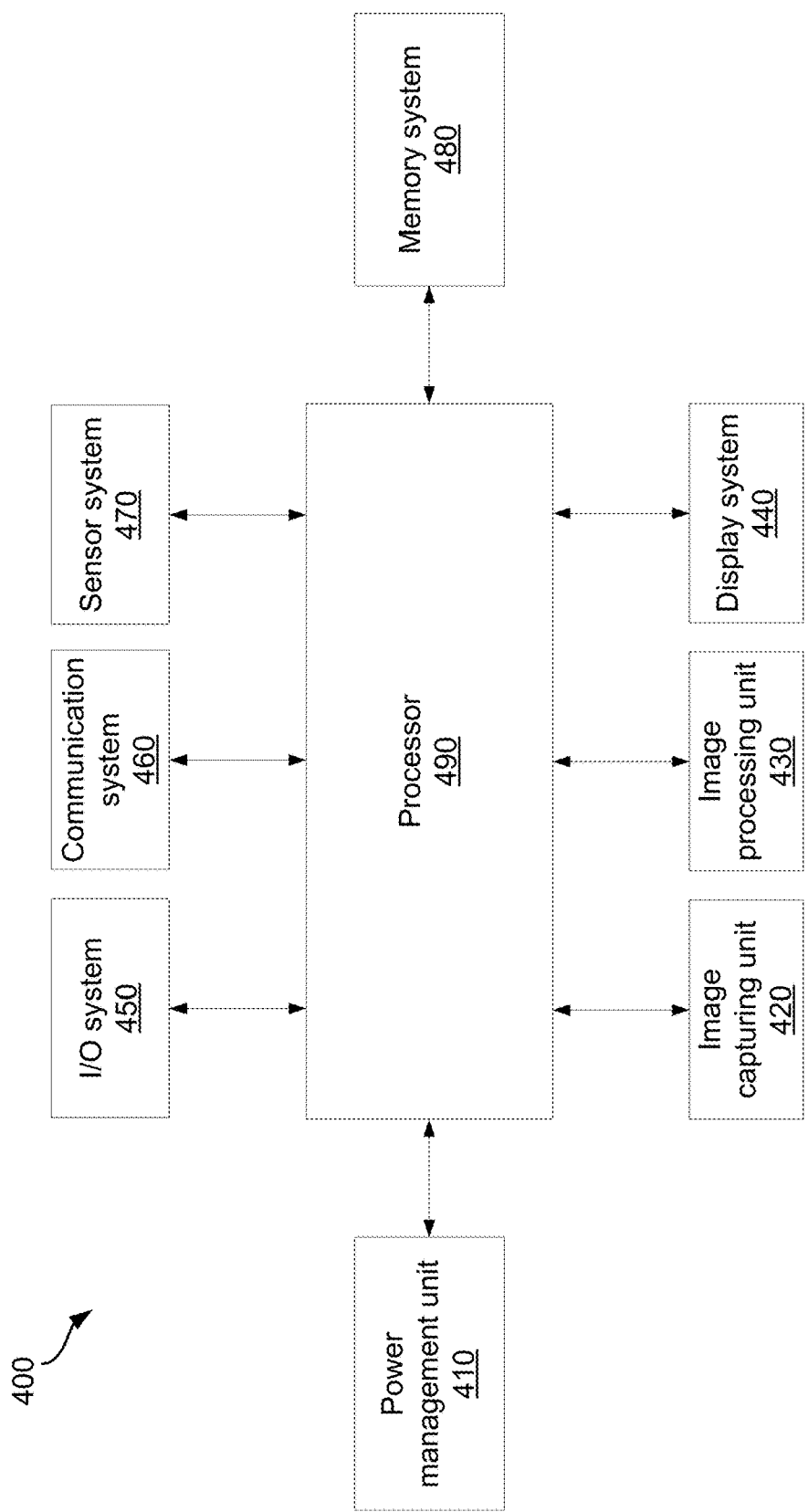
FIG. 4 is a block diagram illustrating various elements of an example device in which several aspects of the present disclosure may be deployed.

FIG. 4 is a block diagram illustrating various elements of an example device in which several aspects of the present disclosure may be deployed. The example device 400 comprises a power management unit 410, an image capturing unit 420, an image processing unit 430, a display system 440, an input/output (I/O) system 450, a communication system 460, a sensor system 470 and a processor 490.

The power management unit 410 is configured to manage and distribute power to the device 400 to perform desired operation. It may comprise at least one of batteries, internal circuitry, integrated circuits and other functional modules to provide power to various components of the device 400. The I/O system 450 helps in exchange of information, data or commands to and from the device 400 with external systems or a user. It comprises at least one of keypad, touch screen, USB ports, wireless ports, smart chip interface, and other control devices.

The display system 440 is a graphical user interface that provides visual output to the user or operator of the device 400. It comprises display devices, but is not limited to, a display screen capable of displaying pictures, videos, 3D pictures and videos, LED status indicators, together with their associated drivers and ancillary components.

The image capturing unit 420 is configured to provide a digital data by recording or capturing an image. The image capturing unit comprises, but is not limited to a lens, lens shutter, image sensor, flash, together with associated drivers and ancillary components. The image processing unit 430 is configured to process the captured image for determining normal and abnormal regions from the image. The processing unit 430 comprises an image processor which performs various operations such as, but not limited to classification, noise reduction, image sharpening, feature extraction, pattern recognition, projection, image editing and restoration.

The sensor system 470 helps in determining status and conditions around the device 400. It comprises sensors, but is not limited to sensors for measuring temperature, humidity, ambient light, motion, torque, orientation and the like. The communication system 460 is configured to establish communication between the device 400 and external system or device through either wired or wireless communication channels. In an embodiment, the wireless communication channels use at least one of communication standards such as, but not limited to, GSM, CDMA, GPRS, Wi-Fi, LAN and Bluetooth.

The processor 490 is configured to provide instructions and to efficiently perform specific tasks comprising various mathematical and control operations. It comprises one or more processors to execute multiple operations either separately or simultaneously.

FIG. 5A is a schematic diagram illustrating the device 501 comprising primary unit 503 and the secondary unit 505 facilitating screening of the cancer cervix in an embodiment of the present disclosure. As shown there, the secondary unit 505 is coupled to the primary unit 501 by means of supporting rods (510A & 510B) in such a way that the device 501 temporarily ceases the direct vision through the primary unit 503. In an embodiment, the outer shield of the secondary unit 505 comprising the image capturing unit is further covered with a protective cover to avoid direct contact with body fluids.

In another embodiment, the secondary unit 505 is easily detachable from the primary unit 503 while not in use to reduce total weight of the device 501 providing more comfort to the patient. Also this ensures same orientation and position of the primary unit 503 without causing discomfort to the patient while screening of the cancer cervix. In yet another embodiment, the secondary unit 505 may temporarily be attached or detached from the primary unit 503 further ensuring more comfort to the patient as well as easy handling and maintenance to operator of the device 501. This helps in using the device 501 easily before and after application of the chemical substance without causing disturbance to orientation or position of the primary unit 503 for examining abnormalities in the cervix region.

Figure 5C:
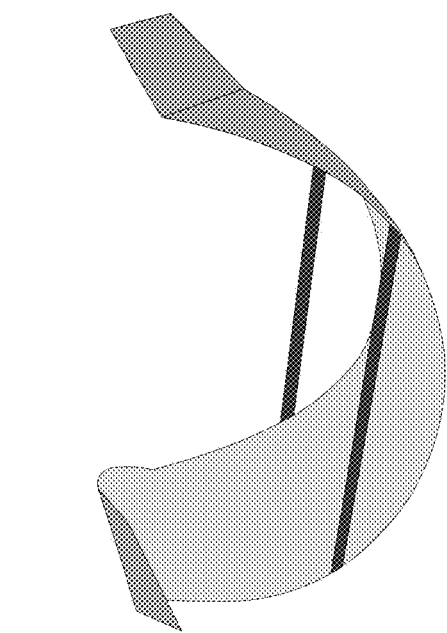
FIG. 5B through FIG. 5D are the schematic diagrams illustrating the coupling of primary unit and the secondary unit by using a detachable holder in an embodiment of the present disclosure.
Figure 5D:
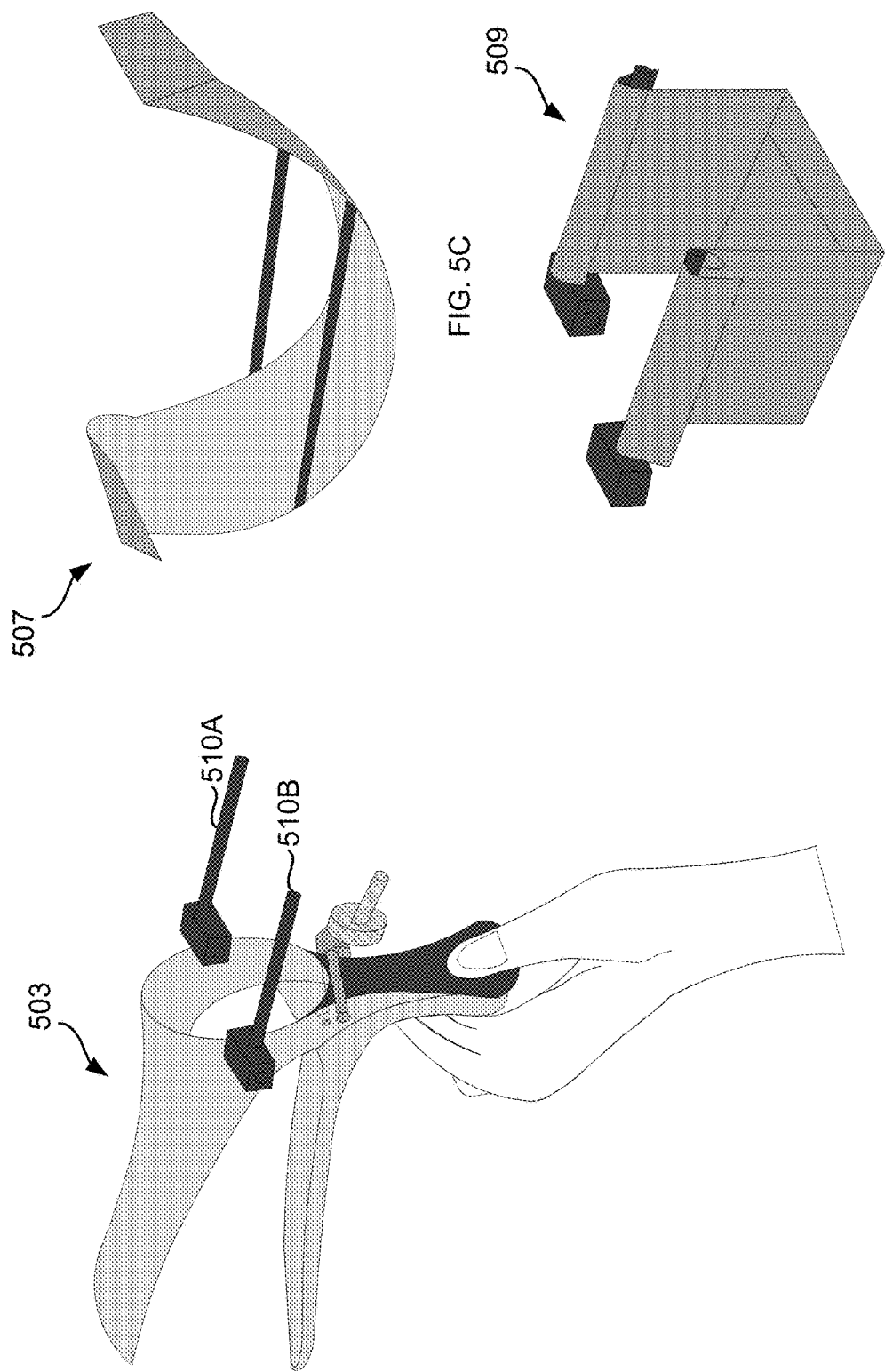
Figure 5B:
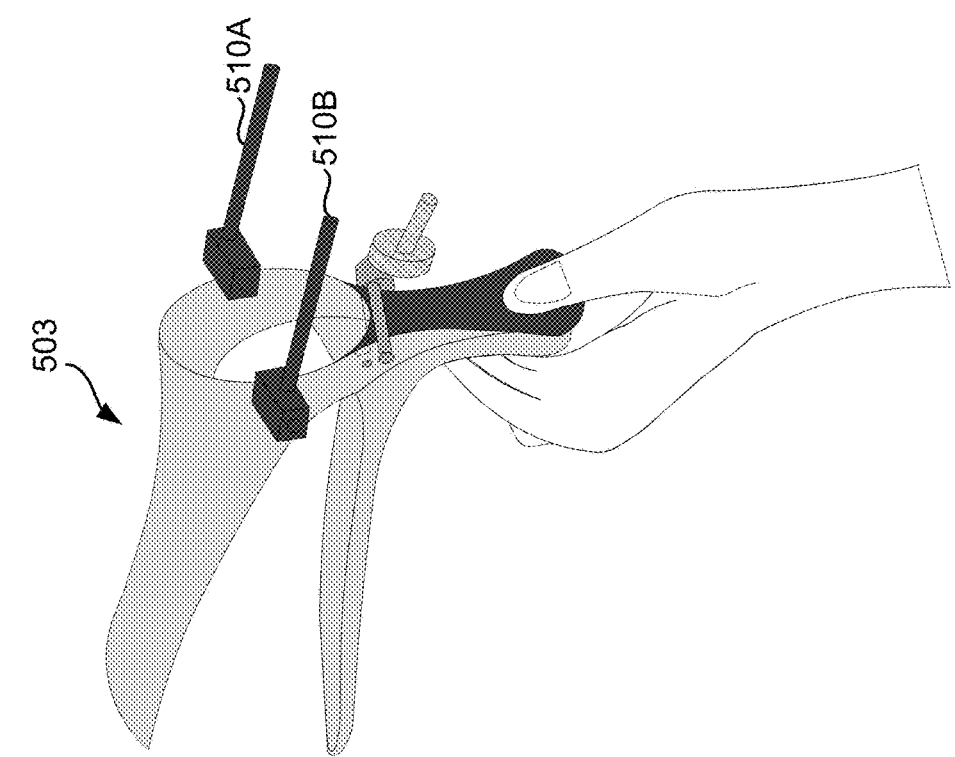

FIG. 5B through FIG. 5D are the schematic diagrams illustrating coupling of the primary unit 503 and the secondary unit 505 by using a detachable holder (507 & 509) in an embodiment of the present disclosure. As shown in the FIG. 5B, the primary unit 503 is coupled with a pair of supporting rods (510A & 510B) on both sides protruding outside. These supporting rods (510A & 510B) host the secondary unit 505 that helps in screening cervical cancer. The secondary unit 505 is mounted on the rods in such a way that it is detachable from the primary unit 503 as per requirement.

As shown in the FIGS. 5C and 5D, a detachable holder (507 & 509) is mounted onto the supporting rods (510A & 510B) which hold the secondary unit 505 firmly to facilitate screening of the cancer cervix. The secondary unit 505 is covered with disposable thin covering for example, polythene sheet or any soft cloth material over the rods (510A & 510B) in a desired shape (say circular or square) that matches to the shape of the secondary unit or the detachable holder (507 & 509).

FIG. 6A through 6C are the schematic diagrams illustrating an exemplary setup of the device in another embodiment of the present disclosure. As shown there, a pair of supporting rods (610A & 610B) is secured to the sides of the primary unit 601 by using a screw 620 or any conventional mechanical means. In an embodiment, the supporting rods 610A and 610B are of horizontal and square shaped rods protruding away from the primary unit 601. Further each of the supporting rods (610A and 610B) comprises at least one square U shaped groove 640 for mounting a detachable holder 603.

FIG. 6B is a schematic diagram illustrating the detachable holder 603 that is to be attached or mounted on the supporting rods 610A and 610B of the primary unit 601. In an embodiment, the detachable holder 603 is provided with a pair of square shaped hook like extensions 630A and 630B on its front side that matches to the size and shape of the groove 640 on the supporting rods 610A and 610B of the primary unit 601. FIG. 6C illustrates setup of the detachable holder 603 and the primary unit 601 in an embodiment of the present disclosure. As shown there, the detachable holder 603 is mounted on the primary unit 601 by fixing the extensions 630A and 630B onto the groove 640 of the supporting rods 610A and 610B. The detachable holder 603 is further provided with a housing to hold the secondary unit for determining abnormalities in the cervix region.

FIG. 7A through 7C are the schematic diagrams illustrating another exemplary setup of the device in yet another embodiment of the present disclosure. FIG. 7A illustrates the primary unit 701 comprising L shaped supporting rods 710A and 710B that are extended from the sides of the primary unit 701 above its handle 730.

FIG. 7B illustrates a detachable holder 703 of the device provided with a pair of square shaped extensions 720A and 720B on either sides of the holder 703. As shown in the FIG. 7C, the extensions (720A & 720B) of the detachable holder 703 are mounted on the supporting rods (710A & 710B) of the primary unit 701 firmly. The detachable holder further comprises a compartment to host the secondary unit of the device. In an embodiment, the supporting rods (710A & 710B) and the extensions (720A & 720B) of the device are of square shaped and square U shaped grooves (740A & 740B) are provided on the supporting rods to hold the detachable holder 703 without causing any complications of the secondary unit while using the device. The square shaped supporting rods (710A & 710B) with grooves 740A and 740B helps to lock the extensions (720A & 720B) to hold the detachable holder without any movement. The L shaped supporting rods (710A & 710B) helps to maintain the detachable holder 703 at a substantial distance from the primary unit 701 avoiding direct contact of the secondary unit or detachable holder 703 with body fluids. In another embodiment, the compartment of the holder 703 may be provided with additional fabric like materials to hold the secondary unit rigidly.

Thus the device of the present disclosure provides clear images of the cervix and further provides instantaneous results whether the captured images represent normal cervix or potentially cancerous lesions without a trained manpower requirement.

While various embodiments of the present disclosure have been described above, it should be understood that they have been presented by way of example only, and not limitation. Thus, the breadth and scope of the present disclosure should not be limited by any of the above-discussed embodiments, but should be defined only in accordance with the following claims and their equivalents.

What is claimed is:

1. An apparatus for detecting cervical cancer comprising:
a mechanical structure configured to expose cervical region comprising:
 a first duck-billed blade forming a hollow cylinder at one end and a second duck-billed blade forming a flat end coupled to the first blade to form part of a speculum (101), in that the cervical region is exposed through circular area of the hollow cylinder;
 a pair of "L" shaped rods (710A and 710B) attached to the hollow cylinder part of the first blade such that they are diagonally opposite and symmetric on either side of the cervical region exposed through the hollow cylinder; and
 a detachable holder (603 and 703) with a housing to hold a secondary unit (505) and at least a pair of hooks (630A, 630B and 720A, 720B) disposed symmetrically on either side of its peripheral surface to mount on the pair of "L" shaped rods (710A and 710B), the secondary unit (505) further comprising:
 an image capturing unit (420) for capturing an image of the exposed cervical region through the hollow cylinder;
 a timer to indicate a time for capturing the image;
 a processor (490) to determining presence or absence of the cervix cancer from the image; and
 a visual indicator indicating a status including normal, abnormal, unclear, wherein the detachable holder (603 and 703) and the secondary unit (505) may be mounted on the speculum (101) when the blades are operative to expose the cervix region, thereby reducing the complexity of setting up the apparatus and reducing the weight of the apparatus when cervix region is prepared for capturing the image.

2. The apparatus of claim 1, wherein the mechanical structure comprises:
a handle (730) coupled to the hollow cylinder of the first blade and the flat end of the second blade by a hinge; and
a rotating screw coupled to the handle for securing the first and second blades in a desired position,
wherein pressing the handle (730) towards the flat end of the second duck-billed blade moves the first and second blades to widen vaginal walls and expose cervix region through the hollow cylinder end of the first blade.

3. The apparatus of claim 2, further comprising a acetowhite region detector to detect an acetowhite region (AR) due to reflection of light comprising:
an SGL extractor (214) to extract saturation, green and luminance components from the image to generate a feature image;
a histogram generator to generate a histogram of the feature image;
a standard deviation filter (216) to smoothen the histogram;
a threshold selector to set a threshold value equal to a value on a Gaussian Curve that is less than a mean value of the histogram;
an SR detector (218) identifying a mask area based on a first threshold value; and
a pixel filler (220) assigning the mean value to all pixels in the mask area.

* * * * *